US006924110B2

United States Patent
Antignac et al.

(10) Patent No.: US 6,924,110 B2
(45) Date of Patent: Aug. 2, 2005

(54) NPHS2 GENE INVOLVED IN THE STEROID-RESISTANT NEPHROTIC SYNDROME, PROTEIN ENCODED BY SAID GENE AND DIAGNOSTIC AND THERAPEUTIC USES

(75) Inventors: Corinne Antignac, Paris (FR); Nicolas Boute, Rambouillet (FR)

(73) Assignee: Institut National de la Sante et de la Rescherche Medicale, Paris (FR)

( * ) Notice: Subject to any disclaimer, the term of this patent is extended or adjusted under 35 U.S.C. 154(b) by 0 days.

(21) Appl. No.: 10/199,945

(22) Filed: Jul. 19, 2002

(65) Prior Publication Data

US 2003/0152954 A1 Aug. 14, 2003

Related U.S. Application Data

(63) Continuation of application No. PCT/FR01/00188, filed on Jan. 19, 2001.

(30) Foreign Application Priority Data

Jan. 20, 2000 (FR) .............................. 00 00709

(51) Int. Cl.[7] .............................. C12Q 1/68; C12Q 1/00; C12P 19/34; G01N 33/566; G01N 33/567
(52) U.S. Cl. .............................. 435/6; 435/91.2; 435/4; 436/504; 436/501
(58) Field of Search .............................. 435/6, 4, 91.2, 435/69.1, 320.1; 436/504, 501; 530/350; 536/23.1, 23.5; 514/2, 44

(56) References Cited

PUBLICATIONS

Database Sequence EMBL 'Online!, Access code AI913530, Jul. 30, 1999, Strausberg R.: "EST; H. sapiens kidney cDNA clone IMAGE: 297835" XP002149359.

Boute, N. et al.: "MPHS2, encoding the glomerular protein podocin, is mutated in autosomal recessive steroid–resistant nephrotic syndrome." NATURE GENETICS, vol. 24, No. 4, Apr. 2000, pp. 349–354, XP000946884.

Database EMBL Sequences 'Online!, Accession No. AL160286, Mar. 13, 2000, "Human DNA sequence from clone RP11–545A16" XP002168082.

Fuchshuber, A. et al.: "Mapping a gene (SRN1) to Chromosome 1q25–q31 in idiopathic nephrotic syndrome confirms a distinct entity of autosomal recessive nephrosis." HUM. MOL. GENET., vol. 4, No. 11, Nov. 1995, pp. 2155–2158, XP000946841.

*Primary Examiner*—Olga N. Chernyshev
(74) *Attorney, Agent, or Firm*—Darby & Darby

(57) ABSTRACT

The invention concerns a novel gene, called NPHS2 gene coding for a protein involved in the cortico-resistant nephrotic syndrome, and diagnostic and therapeutic uses of the novel identified nucleotide sequences and amino acids.

32 Claims, 1 Drawing Sheet

Figure 1:
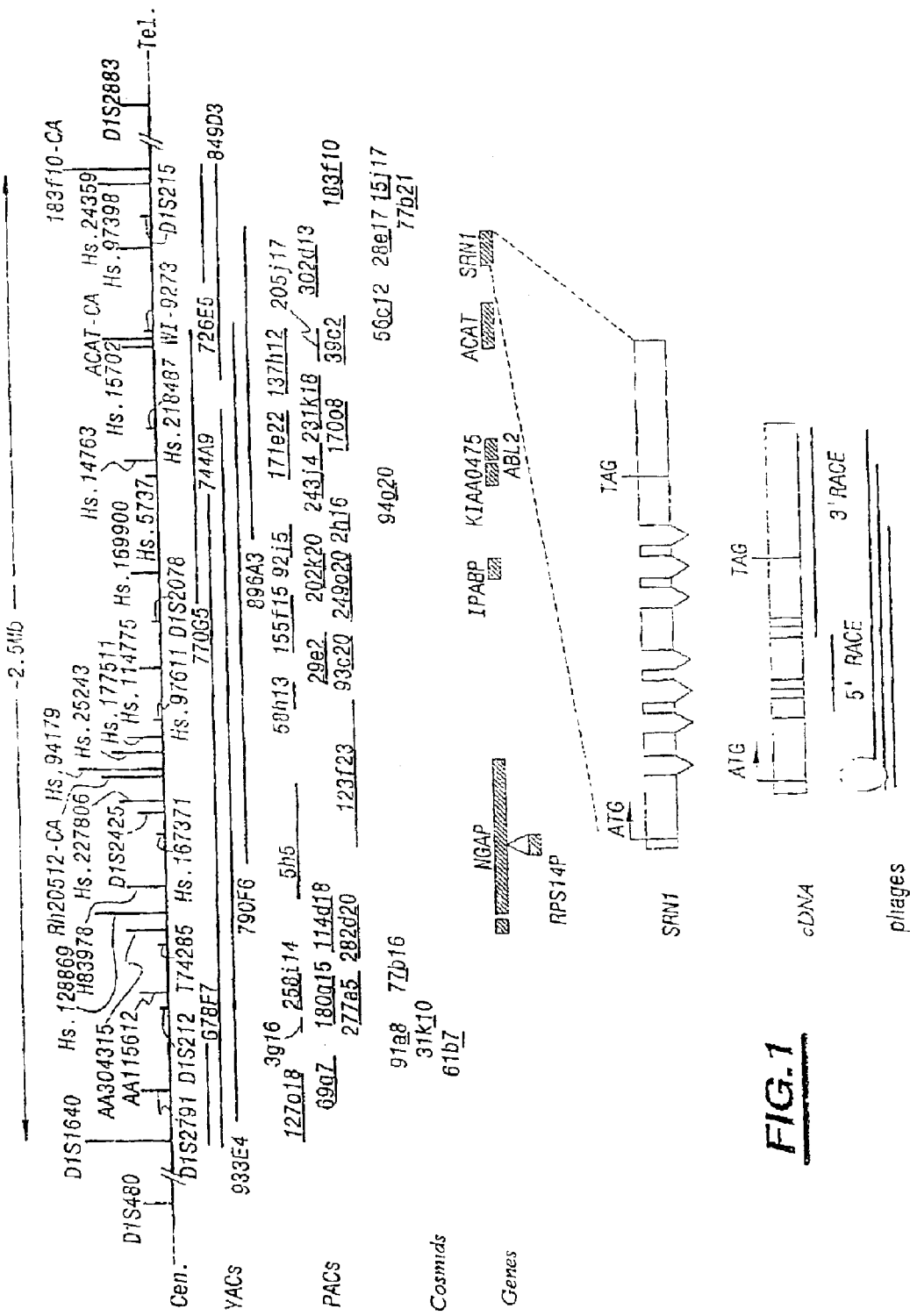

NPHS2 GENE INVOLVED IN THE STEROID-RESISTANT NEPHROTIC SYNDROME, PROTEIN ENCODED BY SAID GENE AND DIAGNOSTIC AND THERAPEUTIC USES

This is a continuation of international application Serial No. PCT/FR01/00188, filed Jan. 19, 2001, the entire disclosure of which is hereby incorporated by reference.

The present invention relates to a novel gene, called NPHS2, which encodes a protein involved in the steroid-resistant nephrotic syndrome.

Idiopathic nephrotic syndrome is a pathological condition which appears mainly in children, and which is characterized by massive proteinurea and nonspecific histological changes in the kidney, sometimes including focal segmental glomerulosclerosis (FSGS). These characteristics are associated with a diffuse effacing of the pedicels of podocytes, observed by electron microscopy (Broyer et al., 1998), which reveals nephrotic syndromes whatever their cause. Most cases correspond to steroid-based therapy and have a good prognosis, but approximately 20% are resistant to steroids and progress to terminal renal insufficiency, leading to complete glomerulosclerosis. Reference is then made to steroid-resistant nephrotic syndrome.

The ultrafiltration of macromolecules of the plasma during primary urine formation in the glomerulus is one of the central functions of the human kidney. The structurally complex capillary wall which is responsible for this function is composed of a basal membrane covered with a fenestrated endothelium on its inner surface and with specialized epithelial cells (podocytes) which form pedicels on the outer surface. In a large number of acquired or hereditary diseases, a dysfunctioning of the glomerular filter is observed, resulting in excessive loss of plasma proteins, leading to a nephrotic syndrome and then possibly to terminal renal insufficiency.

The study of genetic diseases which affect the filtration barrier provides useful models for understanding the physiopathology of the glomerular filtration process. Several of these hereditary disorders with proteinurea and nephrotic syndrome have been described. The most severe is the congenital nephrotic syndrome of the Finnish type (CNF), which is an autosomal recessive disease with strong proteinurea in utero, a nephrotic syndrome at birth usually leading to terminal renal insufficiency during the first two years of life. CNF is caused by mutations in the NPHS1 gene (Kestilä, 1998). Moreover, cases of familial proteinurea or of nephrotic syndrome with histological, focal segmental glomerulosclerosis (FSGS) lesions have been described in older patients, in particular having reached adult age. Two genetic loci for autosomal dominant FSGS have been mapped, respectively, on the 19q13 locus close to the locus of the NPHS1 gene (Mathis et al., 1998) and on the 11q21–q22 locus (Winn et al., 1999).

In 1995, a novel steroid-resistant nephrotic syndrome entity for which transmission is autosomal recessive was characterized according to the following criteria: early beginning between three months and five years old, resistance to steroid-based therapy, progression to terminal renal insufficiency before the age of ten, absence of recurrence after renal transplant and absence of any extrarenal disorder. Histologically, only minimal modifications are observed in early biopsies, but FSGS is generally present at subsequent stages. A genetic locus involved in this steroid-resistant nephrotic syndrome has been mapped in the 1q25–q31 region between the markers D1S452 and D1S466, this region extending over approximately 12 cM (Fuchshuber, 1995). This localization has been confirmed by another team (Lench et al., 1998) and, more recently, a linkage to this region has also been demonstrated in a family exhibiting an FSGS beginning at adult age (Tsukaguchi et al., 1999).

The authors of the present invention have now succeeded in precisely identifying a novel gene involved in the steroid-resistant nephrotic syndrome entity described above. This gene was first called SRN1 and was then renamed NPHS2.

A sequence listing is attached, in which the sequence SEQ ID NO: 1 represents the fragment of cDNA of the NPHS2 gene in humans corresponding to the open reading frame (ORF). This ORF contains 1149 bases and encodes a 383 amino acid protein named podocin, the sequence of which is presented in SEQ ID NO: 2.

The sequences SEQ ID NO: 3 to SEQ ID NO: 10 represent fragments of the genomic DNA of the human NPHS2 gene including, respectively, 8 exons (in bold characters in the attached listing), as follows:

SEQ ID NO: 3:
There are 683 base pairs before the ATG. The cDNA clones obtained by screening a human fetal kidney cDNA library (Clontech library cloned into the λgt11 phage) generally begin between bases 615 and 619. There are 274 base pairs from the ATG to the splicing site (exon 1), and then 147 base pairs of intron sequences.

SEQ ID NO: 4:
There are 151 base pairs of intron, then 104 base pairs of coding (exon 2), and then 123 base pairs of intron.

SEQ ID NO: 5:
There are 336 base pairs of intron, then 73 base pairs of coding (exon 3), and then 291 base pairs of intron.

SEQ ID NO: 6:
There are 187 base pairs of intron, then 83 base pairs of coding (exon 4), and then 90 bp of intron.

SEQ ID NO: 7:
There are 250 base pairs of intron, then 204 base pairs of coding (exon 5), and then 195 base pairs of intron.

SEQ ID NO: 8:
There are 367 base pairs of intron, then 56 base pairs of coding (exon 6), and then 169 base pairs of intron.

SEQ ID NO: 9:
There are 327 bp of intron, then 79 base pairs of coding (exon 7), and then 310 base pairs of intron.

SEQ ID NO: 10:
There are 285 base pairs of intron, then 911 base pairs of cDNA sequence up to the polyadenylation site used (exon 8). The stop codon is at position 562, followed by 109 base pairs of additional genomic sequences covering the other potential polyadenylation sites.

The sequences SEQ ID NO: 11 covers part of exon 5, exons 6 and 7 and a large part of exon 8 (from base 1792 of the cDNA).

The sequences SEQ ID NO: 12 to NO: 27 are primers which are of use for amplifying human sequences.

The sequence SEQ ID NO: 28 is the rat podocin cDNA sequence, the sequence SEQ ID NO: 29 being the corresponding amino acid sequence.

A subject of the present invention is therefore an isolated nucleic acid, the sequence of which is chosen from SEQ ID NO: 3 to SEQ ID NO: 10, or a homologous sequence defined as i) a sequence which is identical to at least 70% of the sequence SEQ ID NO: 3 to SEQ ID NO: 10; or ii) a sequence which hybridizes with the sequence SEQ ID NO: 3 to SEQ ID NO: 10, or the sequences complementary thereto, under stringent hybridization conditions.

A subject of the present invention is also an isolated nucleic acid comprising the sequence SEQ ID NO: 1 or 28, or a homologous sequence defined as i) a sequence which is identical to at least 70% of the sequence SEQ ID NO: 1; or ii) a sequence which hybridizes with the sequence SEQ ID NO: 1, or the sequence complementary thereto, under stringent hybridization conditions; or iii) a sequence which encodes the polypeptide, named podocin, as defined above.

Preferably, a homologous nucleotide sequence according to the invention is identical to at least 75% of the sequences SEQ ID NO: 1 or SEQ ID NO: 3 to 10 and 28, more preferably to at least 85%, or to at least 90%.

Preferentially, such a homologous nucleotide sequence hybridizes specifically to the sequences complementary to the sequences SEQ ID NO: 1, SEQ ID NO: 3 to 10 and SEQ ID NO: 28, under stringent conditions. The parameters which define the conditions of stringency depend on the temperature at which 50% of the paired strands separate (Tm).

For sequences comprising more than 30 bases, Tm is defined by the equation: Tm=81.5+0.41(% G+C)+16.6 Log (concentration of cations)−0.63(% formamide)−(600/number of bases) (Sambrook et al., 1989).

For sequences less than 30 bases in length, Tm is defined by the equation: Tm=4(G+C)+2(A+T).

Under suitable stringency conditions, at which aspecific sequences do not hybridize, the hybridization temperature is approximately 5 to 30° C., preferably 5 to 10° C., below Tm, and the hybridization buffers used are preferably solutions of high ionic strength, such as a 6×SSC solution for example.

A nucleotide sequence homologous to the ORF represented in SEQ ID NO: 1 or 28 includes any nucleotide sequence which differs from the sequence SEQ ID NO: 1 or 28 by mutation, insertion, deletion or substitution of one or more bases, or by the degeneracy of the genetic code, provided that it encodes a polypeptide which has the biological activity of podocin, as defined below.

Included among such homologous sequences are the sequences of the genes, encoding podocin, of mammals other than humans, preferably of a primate, or of a bovine, a member of the sheep family or a pig, or else of a rodent, and also the allelic variants or polymorphic sequences.

The table below gives a certain number of polymorphisms identified in the NPHS2 gene:

| Exon | Polymorphism | Position on the sequences listed |
|---|---|---|
| 1 | −51/ATG T > G | +19 on SEQ ID n° 1 |
|  | nt 102 (G > A) = G34G | +171 on SEQ ID NO: 1 |
| 2 | nt 288 (G > T) = S96S | +357 on SEQ ID NO: 1 |
| 5 | nt 686 (G > A) = R229Q | +755 on SEQ ID NO: 1 |
| 7 | 873 +7 A > G | +413 on SEQ ID NO: 9 |
| 8 | nt 954 (T > C) = A318A | +1023 on SEQ ID NO: 1 |
|  | nt 1038 (A > G) = L346L | +1107 on SEQ ID NO: 1 |

Polymorphisms identified in the NPHS2 gene

A subject of the present invention is also an isolated polypeptide, named podocin, comprising the amino acid sequence SEQ ID NO: 2 or 29, or a homologous sequence defined as i) a sequence which is identical to at least 70% of the sequence SEQ ID NO: 2 or 29; or ii) a sequence which is encoded by a homologous nucleic acid sequence as defined in claim 2 ii), i.e. a nucleic acid sequence which hybridizes with the sequence SEQ ID NO: 2 or 29, or the sequence complementary thereto, under stringent hybridization conditions.

More generally, the expression "homologous amino acid sequence" is intended to mean any amino acid sequence which differs from the sequence SEQ ID NO: 2 or 29 by substitution, deletion and/or insertion of an amino acid or of a small number of amino acids, in particular by substitution of natural amino acids with unnatural amino acids or pseudoamino acids, at positions such that these modifications do not significantly harm the biological activity of the podocin. Said substitutions are preferably conservative substitutions, i.e. substitutions of amino acids of the same class, such as substitutions of amino acids with uncharged side chains (such as asparagine, glutamine, serine, threonine and tyrosine), of amino acids with basic side chains (such as lysine, arginine and histidine), of amino acids with acid side chains (such as aspartic acid and glutamic acid), or amino acids with apolar side chains (such as glycine, alanine, valine, leucine, isoleucine, proline, phenylalanine, methionine, tryptophan and cysteine).

Preferably, such a homologous amino acid sequence is identical to at least 85% of the sequence SEQ ID NO: 2 or 29, preferably to at least 95%.

Homology is generally determined using a sequence analysis program (for example, Sequence Analysis Software Package of the Genetics Computer Group, University of Wisconsin Biotechnology Center, 1710 University Avenue, Madison, Wis. 53705). Similar amino acid sequences are aligned so as to obtain the maximum degree of homology (i.e. identity). For this purpose, it may be necessary to artificially introduce gaps into the sequence. Once the optimal alignment has been produced, the degree of homology (i.e. identity) is established by recording all the positions for which the amino acids of the two compared sequences are identical, relative to the total number of positions.

The expression "the biological activity of podocin" refers to the maintaining of the integrity of the glomerular filter. An absence or a detrimental modification of podocin causes the leaking of proteins at the level of the glomerulus and, consequently, the appearance of proteinurea.

The polypeptide of the present invention may be synthesized using all the methods well known to those skilled in the art. The polypeptide of the invention may, for example, be synthesized using synthetic chemistry techniques, such as synthesis of the Merrifield type, which is advantageous for reasons of purity, of antigenic specificity and of absence of undesirable byproducts, and for its ease of production.

A recombinant podocin may also be produced using a method in which a vector containing a nucleic acid comprising the sequence SEQ ID NO: 1 or no 28, or a homologous sequence, is transferred into a host cell which is cultured under conditions which allow the expression of the corresponding polypeptide.

The podocin produced may then be recovered and purified.

The purification methods used are known to those skilled in the art. The recombinant polypeptide obtained may be purified from cell lysates and extracts and/or from the culture medium supernatant, via methods used individually or in combination, such as fractionation, chromatography methods, immunoaffinity techniques using specific mono- or polyclonal antibodies, etc.

The nucleic acid sequence of interest, encoding podocin, may be inserted into an expression vector, in which it is functionally linked to elements for regulating the expression thereof, such as in particular transcription promoters, activators and/or terminators.

The signals controlling the expression of the nucleotide sequences (promoters, activators, termination sequences, etc.) are chosen as a function of the cellular host used. To this effect, the nucleotide sequences according to the invention may be inserted into vectors which replicate autonomously in the host chosen, or vectors which integrate into the host chosen. Such vectors will be prepared according to the methods commonly used by those skilled in the art, and the clones resulting therefrom may be introduced into a suitable host using standard methods, such as, for example electroporation or calcium phosphate precipitation.

The cloning and/or expression vectors as described above, containing one of the nucleotide sequences defined according to the invention, are also part of the present invention.

The invention is also directed toward the host cells transfected, transiently or stably, with these expression vectors. These cells may be obtained by introducing, into procaryotic or eucaryotic host cells, a nucleotide sequence inserted into a vector as defined above, and then culturing said cells under conditions which allow replication and/or expression of the nucleotide sequence transfected.

Examples of host cells include, in particular, mammalian cells, such as COS-7, 293 or MDCK cells, insect cells, such as SF9 cells, bacteria, such as *E. coli*, and yeast strains, such as YRG2.

The various nucleotide sequences of the invention may or may not be of artificial origin. They may be DNA or RNA sequences, obtained by screening sequence libraries using probes developed on the basis of the sequences SEQ ID NO: 1 or 28 and 3 to 10. Such libraries may be prepared using conventional molecular biology techniques known to those skilled in the art.

The nucleotide sequences according to the invention may also be prepared by chemical synthesis, or by mixed methods including chemical or enzymatic modification of sequences obtained by screening libraries.

These nucleotide sequences make it possible to prepare probes or primers which hybridize specifically with a sequence SEQ ID NO: 1 or 28, or 3 to 10, according to the invention, or the strand complementary thereto. Suitable hybridization conditions correspond to the conditions of temperature and of ionic strength usually used by those skilled in the art, preferably under stringent conditions as defined above. These probes may be used as an in vitro diagnostic tool, for detecting, via hybridization experiments, in particular "in situ" hybridization experiments, transcripts specific for the polypeptide of the invention in biological samples, or for demonstrating aberrant syntheses or genetic abnormalities resulting from a polymorphism, from mutations or from incorrect splicing.

The nucleic acids of the invention which are of use as probes comprise a minimum of 10 nucleotides, preferentially at least 20 nucleotides, more preferentially at least 100 nucleotides. The nucleic acids which are of use as primers comprise a minimum of 10 nucleotides, preferably at least 14 nucleotides, and preferentially less than 40 nucleotides.

More precisely, a subject of the present invention is a nucleic acid having at least 10 nucleotides, which hybridizes specifically with one of the nucleic acid sequences SEQ ID NO: 1 or 28, or 3 to 10, or the sequence complementary thereto, under stringent hybridization conditions.

Advantageously, use may be made, as a probe, of the nucleic acid consisting of the sequence SEQ ID NO: 11, which covers part of exon 5, exons 6 and 7 and a large part of exon 8 (from base 728 to base 1792 of the cDNA).

Moreover, the nucleic acids consisting of the sequences SEQ ID NO: 12 to SEQ ID NO: 27 may be used as a primer for an amplification (for example by PCR).

Preferentially, the probes or primers of the invention are labeled prior to their use. For this, several techniques are within the scope of those skilled in the art, such as, for example, fluorescent, radioactive, chemiluminescent or enzymatic labeling.

The in vitro diagnostic methods in which these oligonucleotides are used for detecting mutations or genomic rearrangements, in the NPHS2 gene, are included in the present invention.

Those skilled in the art are well aware of the standard methods for analyzing the DNA contained in a biological sample and for diagnosing a genetic disorder. Many strategies for genotypic analysis are available (Antonarakis et al., 1989; Cooper et al., 1991).

Preferably, use may be made of the DGGE (denaturing gradient gel electrophoresis) method, the SSCP (single strand confirmation polymorphism) method or the DHPLC (denaturing high performance liquid chromatography; Kuklin et al., 1997; Huber et al., 1995) method, for detecting an abnormality in the NPHS2 gene. Such methods are preferably followed by direct sequencing. The RT-PCR method may advantageously be used to detect abnormalities in the NPHS2 transcript, since it makes it possible to visualize the consequences of a splicing mutation which causes the loss of one or more exons in the transcript, or an aberrant splicing due to the activation of a cryptic site. This method is also preferably followed by direct sequencing. The most recently developed methods using DNA chips may also be used to detect an abnormality in the NPHS2 gene (Bellis et al., 1997).

The cloning of the NPHS2 gene and also the identification of various mutations responsible for the steroid-resistant nephrotic syndrome make it possible to envision direct diagnoses. The specificity and reliability of such methods for diagnosis are particularly appreciable for prenatal diagnosis. The nucleic acid sequences of the present invention therefore represent a particularly advantageous tool for genetic counsel.

A subject of the present invention is therefore the use of at least one nucleic acid as defined above, for detecting an abnormality in the NPHS2 gene, defined as comprising a nucleic acid sequence SEQ ID NO: 3 to 10, or in its transcript, defined as comprising a nucleic acid sequence complementary to the sequence SEQ ID NO: 1.

A subject of the invention is, consequently, a method for the in vitro diagnosis of a steroid-resistant nephrotic syndrome related to a mutation of the NPHS2 gene, comprising the steps consisting in:

a1) placing a biological sample containing DNA together with specific oligonucleotides for amplifying all or part of the NPHS2 gene, defined as comprising a nucleic acid sequence chosen from SEQ ID NO: 3 to 10, or a homologous sequence;

b1) amplifying said DNA;

c1) detecting the amplification products;

d1) comparing the amplification products obtained with those obtained using a control sample, and detecting in this way a possible abnormality in said NPHS2 gene, indicating a steroid-resistant nephrotic syndrome related to a mutation of the NPHS2 gene; or, according to an alternative, a2) placing a biological sample containing RNA together with specific oligonucleotides for amplifying all or part of the transcript of the NPHS2 gene, defined as comprising a nucleic acid sequence complementary to the sequence SEQ ID NO: 1 or a homologous sequence;

b2) amplifying said DNA;

c2) detecting the amplification products;

d2) comparing the amplification products obtained with those obtained using a control sample, and detecting in this way a possible abnormality in said transcript of the NPHS2 gene, indicating a steroid-resistant nephrotic syndrome related to a mutation of the NPHS2 gene.

The isolated nucleic acids comprising a sequence which differs from the sequence SEQ ID NO: 1 by a mutation, insertion or deletion, in particular in at least one of the positions of nucleotides 481, 173/174, 488, 924/925, 128, 343, 482, 548, 607 and 940, or else 1033, 529, 622, 774–782, 154, 422, 442, 571, 572, 583, 783, 794 and 848, are also part of the invention.

Among the mutations already identified, the following, given in tables 1 and 2, are in particular noted.

These tests can in particular be exploited in families which already have an affected child, for presymptomatic diagnosis (in particular prenatal diagnosis).

In sporadic cases, the detection of a mutation of the NPHS2 gene makes it possible to modify the treatment (and in particular to avoid immunosuppressive treatments which will be ineffective) and to predict a lack of recurrence after renal transplant.

This diagnostic test may also be used to investigate the association of certain polymorphic variants of podocin in other pathological conditions with secondary involvement of abnormalities of the glomerular filter (diabetic nephropathy, nephropathy in AIDS, nephron loss, arterial hypertension). These variants may represent factors of sus-

TABLE 1

Mutations in the NPHS2 gene

| Type of mutation[a] | Nucleotide change | Effect on the coding sequence | Exon | Identification n° of the family concerned | Mutation status[b] | Position on SEQ ID NO: 1 |
|---|---|---|---|---|---|---|
| Nonsense | C → T at 412 | R138X | 3 | 8 | H | 481 |
| Deletion/ insertion | Insertion of G at 104/5 | Frameshift | 1 | 14 | H | 173/174 |
| | Deletion of G at 419 | Frameshift | 3 | 14 | H[c] | 488 |
| | Deletion of AA at 855/6 | Frameshift | 7 | 9 | h | 924/925 |
| Missense | C → T at 59 | P20L | 1 | 15 | H | 128 |
| | G → T at 274 | G92C | 1 | 3 | h[c,d] | 343 |
| | G → A at 413 | R138Q | 3 | 4 | h[c] | 482 |
| | | | | 6 | H | |
| | | | | 7 | H | |
| | | | | 11 | H | |
| | | | | 12 | h | |
| | | | | 13 | H | |
| | A → C at 479 | D160G | 4 | 16 | H | 548 |
| | G → A at 538 | V180M | 5 | 10 | H | 607 |
| | | | | 12 | h | 940 |
| | C → T at 871 | R291W | 7 | 2 | h[c] | |

[a] the position of the mutations is indicated by taking the A of the ATG codon to be base 1, and according to the nomenclature of Antonarakis et al.
[b] H = homozygous mutation; h = heterozygous mutation
[c] only the paternal mutation detected
[d] involves the last nucleotide of exon 1 and therefore probably also modifies the splicing
The mutations were not found in 40 controls

TABLE 2

Other mutations in the NPHS2 gene

| Type of mutation | Nucleotide change[a] | Effect on the coding sequence | Exon | Number of families | Mutation status[b] | Position on SEQ ID NO: 1 |
|---|---|---|---|---|---|---|
| Nonsense | C → T at 964 | R322X | 8 | 1 | h | 1033 |
| Deletion/ insertion | Insertion T at 460 | Frameshift | 4 | 1 | h | 529 |
| | Deletion T 553 | Frameshift | 5 | 1 | h[c] | 622 |
| | Deletion 9bp at 705–713 | Deletion TER236–238 | 5 | 1 | H | 774–782 |
| Missense | G → A at 85 | A29T | 1 | 11 | h | 154 |
| | C → T at 353 | P118L | 2 | 1 | h | 422 |
| | G → A at 373 | A125I | 2 | 1 | h | 442 |
| | C → A at 502 | R168S | 4 | 1 | h | 571 |
| | C → T at 502 | R168C | 4 | 1 | h | 571 |
| | G → A at 503 | R168H | 4 | 1 | h | 572 |
| | C → G at 514 | L172V | 4 | 1 | h | 583 |
| | G → T at 714 | R238S | 5 | 1 | h | 783 |
| | C → T at 725 | A242V | 5 | 2 | h | 794 |
| | T → A at 779 | V260E | 6 | 2 | H | 848 |

[a] the position of the mutations is indicated by taking the A of the ATG codon to be base 1, and according to the nomenclature of Antonarakis et al.
[b] H = homozygous mutation; h = heterozygous mutation
The mutations were not found in 40 controls.

ceptibility to the triggering or to the progression of the nephropathy in these diseases.

A subject of the invention is also antibodies directed against the podocin polypeptide as defined above.

They may be poly- or monoclonal antibodies, or fragments thereof, or chimeric antibodies, in particular humanized or immunoconjugated antibodies.

The polyclonal antibodies may be obtained from the serum of an animal immunized against a polypeptide according to the usual procedures.

According to one embodiment of the invention, a suitable peptide fragment, which may be coupled via a reactive residue to a protein or to another peptide, may be used as an antigen. Rabbits are immunized with the equivalent of 1 mg of the peptide antigen according to the procedure described by Benoit et al. (1982). At four-week intervals, the animals are given injections of 200 µg of antigen and bled 10 to 14 days later. After the third injection, the antiserum is examined in order to determine its ability to bind to the antigenic peptide radiolabeled with iodine, which is prepared by the chloramine-T method, and is then purified by chromatography on a carboxymethylcellulose (CMC) ion exchange column. The antibody molecules are then recovered from the mammals and isolated to the desired concentration by methods well known to those skilled in the art, for example using DEAE Sephadex to obtain the IgG fraction.

In order to increase the specificity of the polyclonal serum, the antibodies may be purified by immunoaffinity chromatography using solid-phase immunizing polypeptides. The antibody is brought into contact with the solid-phase immunizing polypeptide for a sufficient period of time so as to cause the polypeptide to immunoreact with the antibody molecule in order to form a solid-phase immunocomplex.

By way of example, polyclonal antibodies in rabbits were produced against two recombinant proteins comprising the fragments of amino acids 15 to 89 and 135 to 383 of podocin, coupled to six histidine residues on the N-terminal side, the cDNAs having been subcloned into the vector PQ E32 (Quiagen) and expressed in *E. coli*.

Monoclonal antibodies may be obtained according to the conventional method for culturing hybridomas described by Köhler and Milstein (1975).

The antibodies or antibody fragments of the invention may, for example, be chimeric antibodies, humanized antibodies, Fab fragments and F(ab')2 fragments. They may also be in the form of labeled antibodies or immunoconjugates.

The antibodies of the invention, in particular the monoclonal antibodies, may especially be used for the immunohistochemical analysis of podocin on specific tissue sections, for example by immunofluorescence, gold labeling, immunoperoxidase, etc.

The antibodies thus produced may advantageously be used in any situation in which the expression of podocin must be observed.

A subject of the invention is also the use of at least one antibody thus produced, for detecting or purifying a polypeptide as defined above in a biological sample.

More precisely, the invention relates to an in vitro method for detecting or measuring the level of expression of podocin in a biological sample, comprising bringing at least one antibody as defined above into contact with said biological sample, under conditions which allow the possible formation of specific immunocomplexes between the podocin and said antibody or antibodies, and detecting the specific immunocomplexes possibly formed. The setting up of such a test (of the ELISA type for example) may in particular be of use in searching for the development of anti-podocin antibodies after renal transplant, in certain autoimmune renal diseases, or even in steroid-sensitive nephrotic syndrome.

A subject of the invention is also a kit for carrying out this method, comprising:
  at least one podocin-specific antibody, optionally attached to a support;
  means for revealing the formation or specific antigen/antibody complexes between the podocin and said antibody, and/or means for quantifying these complexes.

A subject of the invention is also a pharmaceutical composition comprising a podocin polypeptide as defined above or a nucleic acid encoding said polypeptide, in combination with a pharmaceutically acceptable vehicle.

The methods of administration, the dosages and the pharmaceutical forms of the pharmaceutical compositions according to the invention, containing at least one polypeptide, may be determined in the usual way by those skilled in the art, in particular according to the criteria generally taken into account in establishing a therapeutic treatment suitable for a patient, such as, for example, the age or body weight of the patient, the seriousness of his or her general condition, the tolerance to the treatment, and the side effects noted, etc.

In general, a therapeutically or prophylactically effective amount ranging from approximately 0.1 µg to approximately 1 mg may be administered to human adults.

A subject of the invention is also a pharmaceutical composition comprising a nucleic acid as defined above, encoding a polypeptide with podocin activity, and a pharmaceutically acceptable vehicle, said composition being intended to be used in gene therapy. The nucleic acid, preferably inserted into a generally viral vector (such as adenoviruses and retroviruses), may be administered in naked form, free of any vehicle promoting transfer to the target cell, such as anionic liposomes, cationic lipids, microparticles, for example gold microparticles, precipitating agents, for example calcium phosphate, or any other agent facilitating transfection. In this case, the polynucleotide may simply be diluted in a physiologically acceptable solution, such as a sterile solution or a sterile buffer solution, in the presence or absence of a vehicle.

Alternatively, a nucleic acid of the invention may be associated with agents which facilitate transfection. It may, inter alia, be (i) associated with a chemical agent which modifies cellular permeability, such as bupivacaine; (ii) encapsulated in liposomes, optionally in the presence of additional substances which facilitate transfection; or (iii) associated with cationic lipids or microparticles made of silica, of gold or of tungsten.

When the nucleic acid constructs of the invention cover microparticles, these microparticles may be injected intradermally or intraepidermally using the gene gun technique (WO 94/24263).

The amount to be used as a medicinal product depends in particular on the nucleic acid construct itself, on the individual to which this nucleic acid is administered, on the method of administration and the type of formulation, and on the pathological condition. In general, a therapeutically or prophylactically effective amount ranging from approximately 0.1 µg to approximately 1 mg, preferably from approximately 1 µg to approximately 800 µg, and preferentially from approximately 25 µg to approximately 250 µg, can be administered to human adults.

The nucleic acid constructs of the invention may be administered via any conventional route of administration, such as in particular parenterally. The choice of the route of administration depends in particular on the formulation chosen. An administration targeted to the renal tissue, in particular to the glomeruli, may be particularly advantageous.

The polypeptide of the invention, or the nucleic acid encoding this polypeptide, is of use as a medicinal product, especially for the treatment of a renal disease, in particular for the treatment of a steroid-resistant nephrotic syndrome related to a mutation of the NPHS2 gene or occurring in the context of a general disease (AIDS, diabetes, etc.).

Finally, a subject of the invention is therefore a method of therapeutic treatment, in which an effective amount of a podocin polypeptide as defined above or a nucleic acid encoding this polypeptide is administered to a patient requiring such a treatment.

The patient targeted is generally a human, but the application may also be extended to any mammal, where appropriate.

The following examples and also the attached figure illustrate the invention without limiting the scope thereof.

Legend to the Figure

The attached figure is a map of the NPHS2 region. The 2.5 Mb candidate region is delimited by the markers D1S1640 and 183f10-CA. The position on the map of the polymorphic markers, of the STS sequences (in bold characters and italics), of the unique EST sequences and of the UniGene EST clusters (in normal characters) is indicated. The YACs, PACs and cosmids are represented by lines. The genes are indicated by hatched boxes. NGAP is represented by two boxes separated by a horizontal line which symbolizes the presence of the exons which are alternatively spliced in the 5' position probably due to an alternative promoter. RPS14P, a pseudogene of the ribosomal protein S14, is located inside the NGAP intron.

EXAMPLES

Example 1

Identification of the NPHS2 Gene

The approach used by the authors of the present invention in order to identify the NPHS2 gene was to define the minimum genetic interval in which the gene is located, then to establish the physical map of the region by constructing a PAC contig covering the region, to carry out an inventory of the known genes and of the ESTs of the region and to characterize the ESTs (by RACE-PCR and screening a fetal kidney cDNA library).

1 Physical Mapping of the Candidate Region and Localization of the NPHS2 Gene:

A linkage analysis using microsatellite markers (Dib et al., 1996) and also new families of patients made it possible to localize the NPHS2 locus between the markers D1S480 and D1S2883. A YAC contig (20 clones) covering the region between these two markers was constructed. A P1 artificial chromosome (PAC) contig was also constructed so as to cover this region estimated at approximately 3 Mb. It was then possible to characterize other microsatellite markers in this contig. Two families exhibiting the combination events made it possible to precisely localize the locus for the disease between D1S1640 and 183F10CA, a new microsatellite marker identified by sequencing subclones of the region. The 35 PAC contig between these two markers covers approximately 2 to 2.5 Mb, but contains 5 gaps partially filled with 14 cosmids.

The authors of the invention then located on this contig, by searching in the databanks for sequences potentially localized in the region and sequencing the ends of the YACs, of the PACs and of the cosmids, and also of the subclones of various PACs potentially containing CpG islands, genes already known, (UniGene) EST clusters and independent ESTs.

2. Identification of the NPHS2 Gene

In consulting the Sanger Centre database, it was found that the PAC 545A16 contained the marker D1S215 localized close to the telomeric edge of the region of interest, as did the EST AA398634, which came from a testes library and contained short sequences weakly homologous to the stomatin gene, but curiously, a priori, in the direction opposite to the EST. The authors of the invention then localized this EST on the cosmid 28e17 and on the PAC 302d13 and showed, by RT-PCR, that it was expressed in the kidney.

Multiple attempts of RACE-PCR were then necessary in order to obtain a cDNA from this EST. In fact, the products obtained corresponded, in most of the experiments, to genomic DNAs which appeared to be unspliced. However, one of the products obtained corresponded to a transcript containing a short open reading frame and homologous to six ESTs (Unigene cluster Hs. 192657) all originating from a human kidney library, but which had not been localized on the genome. In fact, it so happens that the ESTs of the UniGene cluster Hs. 254975, to which the EST AA398634 belongs, appear to belong to another gene, or pseudogene, the direction of transcription of which is opposite to NPHS2, and which partially overlaps the 3' sequence of NPHS2, which explains the data provided by the databanks relating to the EST AA398634. Using this RACE-PCR product described above as a probe to hybridize a Northern blot containing RNAs from various tissues, it was shown that this transcript of approximately 2 kb was expressed only in the kidney. These results were confirmed by hybridizing a dot blot containing RNAs from 50 different tissues (Clontech). A strong signal was obtained only with adult kidney and fetal kidney. The localization of this gene on the contig and its virtually exclusive expression in the kidney made this gene an excellent candidate gene, this hypothesis being reinforced by the virtual absence of a product of amplification by RT-PCR, using primers located both in the 5' part and in the 3' part of the cDNA, with the terminal kidney-extracted RNA of a patient. The complete cDNA of the NPHS2 gene was cloned by screening a human fetal kidney cDNA library with the probe used to hybridize the Northern Blot (sequence ID NO: 11).

The intron-exon junctions and the genomic sequences upstream of exon 1 were obtained by direct sequencing of the PAC 302d13 and of the cosmid 28e17.

Example 2

Identification of Mutations in Families of Patients

Having characterized the intron-exon structure of the gene, the authors of the invention then sought, by SSCP (Single Strand Conformation Polymorphism), mutations in 16 unrelated patients exhibiting a familial steroid-resistant nephrotic syndrome as described above (early beginning, rapid progression to terminal renal insufficiency, no recurrence after transplant and focal segmental glomerulosclerosis on renal biopsies) and belonging to families in which the study of the haplotypes was compatible with a linkage to the NPHS2 locus.

For this SSCP analysis, the exons were amplified by PCR using flanking intron primers. The PCR conditions and the primers were chosen using the program Oligo 5.0 (NBI), and were as follows:

exon 1, 5'-GCA GCG ACT CCA CAG GGA CT-3' (SEQ ID NO: 12) and 5'-TCA GTG GGT CTC GTG GGG AT-3' (SEQ ID NO: 13);
exon 2, 5'-AGG CAG TGA ATA CAG TGA AG-3' (SEQ ID NO: 14) and 5'-GGC CTC AGG AAA TTA CCT A-3' (SEQ ID NO: 15);
exon 3, 5'-TTC TGG GAG TGA TTT GAA AG-3' (SEQ ID NO: 16) and 5'-TGA AGA AAT TGG CAA GTC AG-3' (SEQ ID NO: 17);
exon 4, 5'-AAG GTG AAA CCC AAA CAG C-3' (SEQ ID NO: 18) and 5'-CGG TAG GTA GAC CAT GGA AA-3' (SEQ ID NO: 19);
exon 5, 5'-CAT AGG AAA GGA GCC CAA GA-3' (SEQ ID NO: 20) and 5'-TTT CAG CAT ATT GGC CAT TA-3' (SEQ ID NO: 21);
exon 6, 5'-CTC CCA CTG ACA TCT GA-3' (SEQ ID NO: 22) and 5'-AAT TTA AAA TGA AAC CAG AA-3' (SEQ ID NO: 23);
exon 7, 5'-CTA AAT CAT GGC TGC ACA CC-3' (SEQ ID NO: 24) and 5'-CTT CCT AAA GGG CAG TCT GG-3' (SEQ ID NO: 25);
exon 8, 5'-GGT GAA GCC TTC AGG GAA TG-3' (SEQ ID NO: 26) and 5'-TTC TAT GGC AGG CCC CTT TA-3' (SEQ ID NO: 27);

at hybridization temperatures of 50° C. (exon 6), 55° C. (exons 2, 3, 4 and 5) and 60° C. (exons 1, 7 and 8). Because of the high GC content of exon 1, the PCR was carried out using Qiagen Taq polymerase and Q-solution according to the manufacturer's instructions. In addition, because of its size, the exon 1 PCR product had to be digested into two fragments with the SmaI enzyme, before the gel electrophoresis. The migration was performed for two hours at 600 V, 25 mA and 15 W with the Genephor Electrophoresis Unit, using the GeneGel Excel 12.5/24 kit (Pharmacia). The staining was carried out with a "GeneStain Automated Gel Stainer" using the PlusOne Silver Staining kit (Pharmacia).

Results

Ten different mutations were observed. Some result in a frameshift or in the appearance of a premature stop codon and are therefore inactivating mutations, which proves that the gene identified is indeed the NPHS2 gene. Others are missense mutations occurring in very conserved regions of the protein, segregating in the families with the disease, and not found in 80 control chromosomes, which strongly suggests that these mutations are indeed responsible for the phenotype in the affected children.

One of the missense mutations (R138Q) was found in six individuals who were not related but who came from the same part of Europe, suggesting the possibility of a founder effect for this mutation.

Example 3

Study of Expression of the NPHS2 Gene in the Kidney by In Situ Hybridization

Method

The paraffin was removed from paraffin-covered 6-µm kidney sections, which were rehydrated and then microwave-treated in sodium citrate buffer (0.01 M, pH 6) in order to increase the hybridization signal. The NPHS2 riboprobes were synthesized from the PCR product of 1065 base pairs (position 728 to 1792 of the NPHS2 cDNA, SEQ ID N° 1) subcloned into the vector PGEM-Teasy. The antisense probe was synthesized, after digestion with SalI, using T7 polymerase and the sense probe was synthesized, after digestion with SacII, using Sp6 polymerase. The riboprobes were labeled either with digoxigenin-11-UTP (Boehringer Mannheim) according to the manufacturer's instructions, or with [$^{35}$S]UTP as described in Sibony et al., 1995. In situ hybridization experiments were carried out as described in Kalatzis et al. (1998) and Heidet et al. (1997) for digoxigenin-11-UTP and [$^{35}$S]UTP probes, respectively.

Results

These in situ hybridization experiments made it possible to show that the NPHS2 gene was expressed only in the podocytes in the mature kidney. In fetal kidneys, no signal was observed at the early stages of development of the nephron. On the other hand, strong signals were detected in the lower segment of the S-shaped body, in the region corresponding to the future podocytes. This expression persists in the immature glomeruli and in the mature glomeruli of the, deep cortex. These results, which show the exclusive expression of the NPHS2 gene in the podocytes, both early during development and in the mature glomeruli, are entirely in agreement with the pathology observed and justify the name "podocin" for the protein encoded by the NPHS2 gene.

Bibliography

Antonarakis S. E., Diagnosis of genetic disorders at the DNA level. N Engl. J. Med. 320:153–163 (1989).

Antonarakis, S. E., Recommendations for a nomenclature system for human gene mutations. Nomenclature Working Group. Hum. Mut. 11, 1–3 (1998).

Bellis et al., medecine/sciences, 13:1317–24, (1997).

Benoit et al., PNAS USA, 79, 917–921 (1982).

Broyer M., Meyrier A., Niaudet P. & Habib R. Minimal changes and focal segmental glomerular sclerosis. In Oxford Textbook of Clinical Nephrology 2$^{nd}$ ed. (eds Davison A. M. et al.) 493–535 (Oxford University Press, Inc., 1998).

Cooper et al., Diagnosis of genetic disease using recombinant DNA, 3$^{rd}$ Edition, Hum Genet., 87:519–560 (1991).

Conton, P. J. et al., Clinical and pathologic features of familial focal segmental glomerulosclerosis. Am. J. Kidney Dis. 26, 34–40 (1995).

Dib, C. et al. A comprehensive genetic map of the human genome based on 5,264 microsatellites. Nature 380, 152–154 (1996).

Fuchshuber, A. et al. Mapping a gene (NPHS2) to chromosome 1q25–q31 in idiopathic nephrotic syndrome confirms a distinct entity of autosomal recessive nephrosis. Hum. Mol. Genet. 4, 2155–2158 (1995).

Heidet, L. et al. Diffuse leiomyomatosis associated with X-linked Alport syndrome: extracellular matrix study using immunohistochemistry and in situ hybridization. Lab. Invest. 76, 233–243 (1997).

Huber, C. G. et al., Rapid and accurate sizing of DNA fragments by ion-pair chromatography on alkylated nonporous poly(styrenedivinylbenzene) particles. Anal. Chem. 67, 578–585 (1995).

Kuklin, A. et al., Detection of single-nucleotide polymorphisms with the WAVE™ DNA fragment analysis system. Genetic Testing 1, 201–206 (1997/98).

Kalatzis, V., Sahly, I., El-Amraoui, A. & Petit, C. Eyal expression in the developing ear and kidney: towards the understanding of the pathogenesis of Branchio-Oto-Renal (BOR) syndrome. Dev. Dyn. 213, 486–499 (1998).

Kestilä, M. et al. Positionally cloned gene for a novel glomerular protein-nephrin-is mutated in congenital nephrotic syndrome. Mol. Cell 1, 575–582 (1998)

Köhler and Milstein, *Nature,* 256, 495–497, (1975).
Lench et al., *Am. J. Hum. Genet.* 63, A296 (1998).
Mathis, B. J. et al. A locus for inherited focal segmental glomerulosclerosis maps to chromosome 19q13. *Kidney. Int.* 53, 282–286 (1998).
Sambrook et al., Molecular cloning, a laboratory manual *Spring Harbor Laboratory Press,* 9.54–62 (1989)

Tsukaguchi et al., Adult onset familial FSGS mapping to chromosome 1q. *J. Am. Soc. Nephrol.* 10, 443A (1999).
Winn, M. P. et al. Linkage of a gene causing familial focal segmental glomerulosclerosis to chromosome 11 and further evidence of genetic heterogeneity. *Genomics* 58, 113–120 (1999).

What is claimed is:

1. A method for diagnosing the presence or absence of steroid resistant nephrotic syndrome in a human, wherein the syndrome is associated with the presence of a mutation in a NPHS2 gene coding for SEQ ID NO: 2, said method comprising detecting the presence or absence of one or more mutations listed in Table 1 and Table 2 in the NPHS2 gene in a biological sample containing nucleic acids obtained from the human, wherein the presence of one or more mutations listed in Table 1 and Table 2 indicates the presence of steroid resistant nephrotic syndrome in the human.

2. The method of claim 1 where the mutation is a nonsense mutation, an insertion or deletion, or a missense mutation.

3. The method of claim 2 wherein the mutation is one or more mutations corresponding to positions 481, 173/174, 488, 924/925, 128, 343, 482, 548, 607, 940, 1033, 529, 622, 774–782, 154, 422, 442, 571, 572, 583, 794, or 848 of SEQ ID NO:1.

4. The method of claim 1 wherein detecting the presence or absence of one or more mutations in a NPHS2 gene coding for SEQ ID NO: 2 comprises:
   a) amplifying nucleic acids of the biological sample containing nucleic acids obtained from the human, thereby obtaining amplification products; and
   b) comparing the amplification products obtained in step a) with amplification products obtained from a control sample containing nucleic acids comprising the NPHS2 gene coding for SEQ ID NO:2,
   wherein if the amplification products from the sample are different from the amplification products of the control, then one or more mutations in the NPHS2 gene in the biological sample containing nucleic acids have been detected.

5. The method of claim 4 wherein the nucleic acids are genomic DNA.

6. The method of claim 5 wherein the NPHS2 gene coding for SEQ ID NO: 2 comprises one or more exons of SEQ ID NOS: 3–10.

7. The method of claim 4 wherein the nucleic acids are RNA.

8. The method of claim 7 wherein the NPHS2 gene coding for SEQ ID NO: 2 comprises the open reading frame of SEQ ID NO: 1.

9. The method of claim 4 wherein amplification is by PCR.

10. The method of claim 9 wherein the PCR amplification uses primers comprising a DNA sequence selected from the group consisting of: SEQ ID NOS: 12–27.

11. The method of claim 4 where the mutation is a nonsense mutation, an insertion or deletion, or a missense mutation.

12. The method of claim 11 wherein the mutation is one or more mutations corresponding to positions 481, 173/174, 488, 924/925, 128, 343, 482, 548, 607, 940, 1033, 529, 622, 774–782, 154, 422, 442, 571, 572, 583, 794, or 848 of SEQ ID NO:1.

13. A method for detecting the presence or absence of a mutation in a NPHS2 gene coding for SEQ ID NO: 2, comprising the steps of:
   a) analyzing a nucleic acid test sample containing the NPHS2 gene for at least one mutation;
   b) comparing results of the analysis of the test sample of step a) with results of the analysis of a control sample, wherein the control sample comprises the NPHS2 gene coding for SEQ ID NO:2; and c) determining the presence or absence of at least one mutation in the test sample.

14. The method of claim 13, wherein the NPHS2 gene coding for SEQ ID NO: 2 comprises the open reading frame of SEQ ID NO: 1.

15. The method of claim 13 wherein the NPHS2 gene coding for SEQ ID NO: 2 comprises one or more exons of SEQ ID NOS: 3–10.

16. The method of claim 13 where the mutation is a nonsense mutation, an insertion or deletion, or a missense mutation.

17. The method of claim 16 wherein the mutation is one or more mutations corresponding to positions 481, 173/174, 488, 924/925, 128, 343, 482, 548, 607, 940, 1033, 529, 622, 774–782, 154, 422,442, 571, 572, 583, 794, or 848 of SEO ID NO:1.

18. The method of claim 13 wherein the NPHS2 gene coding for SEQ ID NO: 2 is amplified prior to analysis.

19. The method of claim 18 wherein the amplification is PCR amplification using primers comprising a DNA sequence selected from the group consisting of: SEQ ID NOS: 12–27.

20. A method for determining whether or not a human is at risk for steroid resistant nephrotic syndrome, wherein the syndrome is associated with the presence of a mutation in a NPHS2 gene coding for SEQ ID NO: 2, said method comprising detecting the presence or absence of one or more mutations listed in Table 1 and Table 2 in the NPHS2 gene coding for SEQ ID NO: 2 in a biological sample containing nucleic acids obtained from the human, wherein the presence of one or more mutations listed in Table 1 or Table 2 indicates that the human is at risk for steroid resistant nephrotic syndrome.

21. The method of claim 20 where the mutation is a nonsense mutation, an insertion or deletion, or a missense mutation.

22. The method of claim 21 wherein the mutation is one or more mutations corresponding to positions 481, 173/174, 488, 924/925, 128, 343, 482, 548, 607, 940, 1033, 529, 622, 774–782, 154, 422, 442, 571, 572, 583, 794, or 848 of SEO ID NO:1.

23. The method of claim 20 wherein detecting the presence or absence of one or more mutations in the NPHS2 gene coding for SEQ ID NO: 2 comprises:
a) amplifying nucleic acids of the biological sample containing nucleic acids obtained from the human, thereby obtaining amplification products; and
b) comparing the amplification products obtained in step a) with amplification products obtained from a control sample containing nucleic acids comprising the NPHS2 gene coding for SEQ ID NO:2,
wherein if the amplification produces from the sample are different from the amplification products of the control, then one or more mutations in the NPHS2 gene in the biological sample containing nucleic acids have been detected.

24. The method of claim 20 wherein the nucleic acids are genomic DNA.

25. The method of claim 24 wherein the NPHS2 gene coding for SEQ ID NO: 2 comprises one or more exons of SEQ ID NOS: 3–10.

26. The method of claim 20 wherein the nucleic acids are RNA.

27. The method of claim 26 wherein the NPHS2 gene coding for SEQ ID NO: 2 comprises the open reading frame of SEQ ID NO: 1.

28. The method of claim 20 wherein amplification is by PCR.

29. The method of claim 28 wherein the PCR amplification uses primers comprising a DNA sequence selected from the group consisting of: SEQ ID NOS: 12–27.

30. The method of claim 23 where the mutation is a nonsense mutation, an insertion or deletion, or a missense mutation.

31. The method of claim 30 wherein the mutation is one or more mutations corresponding to positions 481, 173/174, 488, 924/925, 128, 343, 482, 548, 607, 940, 1033, 529, 622, 774–782, 154, 422,442, 571, 572, 583, 794, or 848 of SEO ID NO:1.

32. The method of claim 23 wherein the nucleic acids are RNA.

* * * * *

UNITED STATES PATENT AND TRADEMARK OFFICE
CERTIFICATE OF CORRECTION

PATENT NO. : 6,924,110 B2 Page 1 of 1
APPLICATION NO. : 10/199945
DATED : August 2, 2005
INVENTOR(S) : Corinne Antignac et al.

It is certified that error appears in the above-identified patent and that said Letters Patent is hereby corrected as shown below:

On Title page item 73
In the Assignee:

Please delete "Institut National de la Sante et de la Rescherche Medicale, Paris (FR)" and substitute with -- Institut National de la Sante et de la Recherche Medicale (Inserm), Paris (FR) --.

Signed and Sealed this

First Day of April, 2008

JON W. DUDAS
*Director of the United States Patent and Trademark Office*

SEQUENCE LISTING

```
<160> NUMBER OF SEQ ID NOS: 29

<210> SEQ ID NO 1
<211> LENGTH: 1853
<212> TYPE: DNA
<213> ORGANISM: Homo sapiens
<220> FEATURE:
<221> NAME/KEY: CDS
<222> LOCATION: (70)..(1221)

<400> SEQUENCE: 1
cacagggact gcgctccctt gccctagcg ctcccgcgct gctgctccag ccgcccggca        60 gctctgagg atg gag agg agg gcg cgg agc tcc tcc agg gag tcc cgc ggg      111
           Met Glu Arg Arg Ala Arg Ser Ser Ser Arg Glu Ser Arg Gly
             1               5                  10 cga ggc ggc agg act ccg cac aag gag aac aag agg gca aag gcc gag        159
Arg Gly Gly Arg Thr Pro His Lys Glu Asn Lys Arg Ala Lys Ala Glu
 15                  20                  25                  30 agg agc ggc ggg ggc cgc ggg cgc cag gag gct ggg ccc gag ccg tcg        207
Arg Ser Gly Gly Gly Arg Gly Arg Gln Glu Ala Gly Pro Glu Pro Ser
                 35                  40                  45 ggc tcc gga cgg gcg ggg acc ccg ggg gag ccc cga gcg ccc gcc gcc        255
Gly Ser Gly Arg Ala Gly Thr Pro Gly Glu Pro Arg Ala Pro Ala Ala
             50                  55                  60 acg gtg gtg gac gtg gat gag gtc cga ggc tcc ggc gag gag ggc acc        303
Thr Val Val Asp Val Asp Glu Val Arg Gly Ser Gly Glu Glu Gly Thr
 65                  70                  75 gag gtg gtg gcg ctg ttg gag agc gag cgg ccc gag gaa ggt acc aaa        351
Glu Val Val Ala Leu Leu Glu Ser Glu Arg Pro Glu Glu Gly Thr Lys
 80                  85                  90 tcc tcc ggc tta ggg gcc tgt gag tgg ctt ctt gtc ctc att tcc ctg        399
Ser Ser Gly Leu Gly Ala Cys Glu Trp Leu Leu Val Leu Ile Ser Leu
 95                 100                 105                 110 ctc ttc atc atc atg acc ttc cct ttt tcc atc tgg ttc tgc gta aag       447
Leu Phe Ile Ile Met Thr Phe Pro Phe Ser Ile Trp Phe Cys Val Lys
                115                 120                 125 gtt gta caa gag tat gaa aga gta att ata ttc cga ctg gga cat ctg        495
Val Val Gln Glu Tyr Glu Arg Val Ile Ile Phe Arg Leu Gly His Leu
                130                 135                 140 ctt cct gga aga gcc aaa ggc cct ggt ctt ttc ttt ttg ccc tgc            543
Leu Pro Gly Arg Ala Lys Gly Pro Gly Leu Phe Phe Phe Leu Pro Cys
            145                 150                 155 ctg gat acc tac cac aag gtt gac ctt cgt ctc caa act ctg gag ata        591
Leu Asp Thr Tyr His Lys Val Asp Leu Arg Leu Gln Thr Leu Glu Ile
            160                 165                 170 cct ttt cat gag atc gtg acc aaa gac atg ttt ata atg gag ata gat        639
Pro Phe His Glu Ile Val Thr Lys Asp Met Phe Ile Met Glu Ile Asp
175                 180                 185                 190 gcc att tgc tac tac cga atg gaa aat gcc tct ctt ctc cta agc agt        687
Ala Ile Cys Tyr Tyr Arg Met Glu Asn Ala Ser Leu Leu Leu Ser Ser
                195                 200                 205
```

-continued

| | | |
|---|---|---|
| ctt gct cat gta tct aaa gct gtg caa ttc ctt gtg caa acc act atg<br>Leu Ala His Val Ser Lys Ala Val Gln Phe Leu Val Gln Thr Thr Met<br>                  210                  215                  220 | 735 |
| aag cgt ctc cta gca cat cga tcc ctc act gaa att ctt cta gag agg<br>Lys Arg Leu Leu Ala His Arg Ser Leu Thr Glu Ile Leu Leu Glu Arg<br>              225                  230                  235 | 783 |
| aag agc atc gcc caa gat gca aag gtt gcc ttg gat tca gtg acc tgt<br>Lys Ser Ile Ala Gln Asp Ala Lys Val Ala Leu Asp Ser Val Thr Cys<br>240                  245                  250 | 831 |
| att tgg gga atc aaa gtg gag aga ata gaa att aaa gat gtg agg ttg<br>Ile Trp Gly Ile Lys Val Glu Arg Ile Glu Ile Lys Asp Val Arg Leu<br>255                  260                  265                  270 | 879 |
| cca gct ggg ctt cag cac tca ctg gct gtg gag gct gaa gcg caa aga<br>Pro Ala Gly Leu Gln His Ser Leu Ala Val Glu Ala Glu Ala Gln Arg<br>                  275                  280                  285 | 927 |
| caa gcc aaa gtg cgg atg att gct gca gaa gcg gaa aag gct gct tct<br>Gln Ala Lys Val Arg Met Ile Ala Ala Glu Ala Glu Lys Ala Ala Ser<br>              290                  295                  300 | 975 |
| gag tcc ctg agg atg gca gct gag att ctg tca ggc acc cct gct gct<br>Glu Ser Leu Arg Met Ala Ala Glu Ile Leu Ser Gly Thr Pro Ala Ala<br>              305                  310                  315 | 1023 |
| gtt cag ctt cga tac ctc cac acc ctt cag tct ctg tcc aca gag aag<br>Val Gln Leu Arg Tyr Leu His Thr Leu Gln Ser Leu Ser Thr Glu Lys<br>              320                  325                  330 | 1071 |
| cct tcc act gtg gtt tta cct ttg cca ttt gac cta ctg aat tgc ctg<br>Pro Ser Thr Val Val Leu Pro Leu Pro Phe Asp Leu Leu Asn Cys Leu<br>335                  340                  345                  350 | 1119 |
| tct tct ccc agc aac aga act cag gga agc ctc ccc ttc cca agt cct<br>Ser Ser Pro Ser Asn Arg Thr Gln Gly Ser Leu Pro Phe Pro Ser Pro<br>                  355                  360                  365 | 1167 |
| tcc aaa cct gtt gag cca cta aat cct aaa aag aaa gac tct ccc atg<br>Ser Lys Pro Val Glu Pro Leu Asn Pro Lys Lys Lys Asp Ser Pro Met<br>                  370                  375                  380 | 1215 |
| tta tag gaaggatggg gcataatgtg actgtaaagg ggcctgccat agaaaagtca<br>Leu | 1271 |
| catccctgag ggagacactc tgtcctcatt ccctgcccct cctttggttg ccatatggaa | 1331 |
| tggccatgga atgcacgaag tcacaatgca ccatccatga aagacrgtg aaatgatgta | 1391 |
| atgacagaga aggcagacaa catgtttccg tgactcatct agtcagagca attatgggaa | 1451 |
| acagctttgg tcaacattct actttggaaa gaattttgag tctagatgtg gttaaatttt | 1511 |
| gacttctggg aacttggttc agatgtccct ttcactgtat gtcctctgac ccctttggca | 1571 |
| aggttgccac agctcccaca gcccttccta caagcaccta tcattgggct tgtcacactc | 1631 |
| tattgctctt ctgtcccgaa gatgcagtct tctctccaat gatactacca agtcttagtt | 1691 |
| ttcctcaacc acactcaatc tttttgctcc accctgaatt cctcacacct aaccctgata | 1751 |
| gttacctaaa gtgacactta aatgtttcag agtgaatgca aaaagagag atgtacttgg | 1811 |
| agtcggatat acaatttatc cctaattaaa gcatttaaaa gg | 1853 |

<210> SEQ ID NO 2
<211> LENGTH: 383
<212> TYPE: PRT
<213> ORGANISM: Homo sapiens

<400> SEQUENCE: 2

Met Glu Arg Arg Ala Arg Ser Ser Ser Arg Glu Ser Arg Gly Arg Gly
 1               5                  10                  15

Gly Arg Thr Pro His Lys Glu Asn Lys Arg Ala Lys Ala Glu Arg Ser

```
                    20                  25                  30
Gly Gly Gly Arg Gly Arg Gln Glu Ala Gly Pro Glu Pro Ser Gly Ser
            35                  40                  45

Gly Arg Ala Gly Thr Pro Gly Glu Pro Arg Ala Pro Ala Ala Thr Val
    50                  55                  60

Val Asp Val Asp Glu Val Arg Gly Ser Gly Glu Glu Gly Thr Glu Val
65                  70                  75                  80

Val Ala Leu Leu Glu Ser Glu Arg Pro Glu Glu Gly Thr Lys Ser Ser
                85                  90                  95

Gly Leu Gly Ala Cys Glu Trp Leu Leu Val Leu Ile Ser Leu Leu Phe
            100                 105                 110

Ile Ile Met Thr Phe Pro Phe Ser Ile Trp Phe Cys Val Lys Val Val
            115                 120                 125

Gln Glu Tyr Glu Arg Val Ile Ile Phe Arg Leu Gly His Leu Leu Pro
130                 135                 140

Gly Arg Ala Lys Gly Pro Gly Leu Phe Phe Phe Leu Pro Cys Leu Asp
145                 150                 155                 160

Thr Tyr His Lys Val Asp Leu Arg Leu Gln Thr Leu Glu Ile Pro Phe
                165                 170                 175

His Glu Ile Val Thr Lys Asp Met Phe Ile Met Glu Ile Asp Ala Ile
            180                 185                 190

Cys Tyr Tyr Arg Met Glu Asn Ala Ser Leu Leu Ser Ser Leu Ala
            195                 200                 205

His Val Ser Lys Ala Val Gln Phe Leu Val Gln Thr Thr Met Lys Arg
    210                 215                 220

Leu Leu Ala His Arg Ser Leu Thr Glu Ile Leu Leu Glu Arg Lys Ser
225                 230                 235                 240

Ile Ala Gln Asp Ala Lys Val Ala Leu Asp Ser Val Thr Cys Ile Trp
                245                 250                 255

Gly Ile Lys Val Glu Arg Ile Glu Ile Lys Asp Val Arg Leu Pro Ala
            260                 265                 270

Gly Leu Gln His Ser Leu Ala Val Glu Ala Glu Ala Gln Arg Gln Ala
        275                 280                 285

Lys Val Arg Met Ile Ala Ala Glu Ala Glu Lys Ala Ala Ser Glu Ser
    290                 295                 300

Leu Arg Met Ala Ala Glu Ile Leu Ser Gly Thr Pro Ala Ala Val Gln
305                 310                 315                 320

Leu Arg Tyr Leu His Thr Leu Gln Ser Leu Ser Thr Glu Lys Pro Ser
                325                 330                 335

Thr Val Val Leu Pro Leu Pro Phe Asp Leu Leu Asn Cys Leu Ser Ser
            340                 345                 350

Pro Ser Asn Arg Thr Gln Gly Ser Leu Pro Phe Pro Ser Pro Ser Lys
        355                 360                 365

Pro Val Glu Pro Leu Asn Pro Lys Lys Lys Asp Ser Pro Met Leu
    370                 375                 380

<210> SEQ ID NO 3
<211> LENGTH: 1104
<212> TYPE: DNA
<213> ORGANISM: Homo sapiens

<400> SEQUENCE: 3
aggatataaa ataagaaata cgtagggagg agagaaaggc atccttgaga cgactccaag      60
aaggaaagtt ggggatgagg cgaaatttct gattttacct taaagtgacc ctaattcgat     120
```

```
gaccttttgt ggttttttc tttttctt tttacttggc cctgcccaag caggacctaa      180
aaacaaacag acaaaaaagg ttactaacaa ctgttcctct ccacgaaaat ctgcagtaaa      240
aggtaaaaga tgtattcgtt ttgaagagaa accagagctt gcgatgagct tctgtatctc      300
cgtcagccct ctagcatgac attaggaacc ctccaggaga tgagtcttca cagcccgggt      360
tggcacctgc agacacgcac ttttcaacgc ccgcaccctg cccggggccg gctctcccac      420
ccaggcctct ctctgcttca gcgccgcccc ggccgtggga gtcggcgggc gcagtccaca      480
gctccaccaa gacacagctg tcggggttcc gggtgcgccc cgcccgcggc cccggtgtcc      540
cgcccctcgc cctcagcccc cacccgacgg tctttagggt ccccgggca cgccacgcgg      600 acccgcagcg actccacagg gactgcgctc ccgtgcccct agcgctcccg cgctgctgct      660
ccagccgccc ggcagctctg aggatggaga ggagggcgcg gagctcctcc agggagtccc      720
gcgggcgagg cggcaggact ccgcacaagg agaacaagag ggcaaaggcc gagaggagcg      780
gcgggggccg cgggcgccag gaggctgggc ccgagccgtc gggctccgga cgggcgggga      840
ccccggggga gccccgagcg cccgccgcca cggtggtgga cgtggattag gtccgaggct      900
ccggcgagga gggcaccgag gtggtggcgc tgttggagag cgagcggccc gaggaaggta      960
cggattcagc accactatct gctacttttc caggtggtaa ctaaggggcg tcagataagg     1020
tggaaagggt catccccacg agacccactg aagccagagc agattgctgg atgctcaggt     1080
tcccaggaac ggaagggcgt aagt                                           1104

<210> SEQ ID NO 4
<211> LENGTH: 378
<212> TYPE: DNA
<213> ORGANISM: Homo sapiens

<400> SEQUENCE: 4
tctgactact ctgatttgac ttattcctaa tatttccagc aaagtctcca agytgtgcca       60
actccaatac caagaattgg accaacagat gctagtcagt gaatacagtg aagtttcaat      120
ataattattg gtttgcttta atttttttaa ggtaccaaat cctccggctt aggggcctgt      180
gagtggcttc ttgtcctcat ttccctgctc ttcatcatca tgaccttccc tttttccatc      240
tggttctgcg taaaggtgag attccataag gacccaatag gtaatttcct gaggcctctc      300
actggccaca ccatgcccat tctcacttct gttttctggt acatgttatt gctccatgtg      360
gaatgccctc accccaga                                                   378

<210> SEQ ID NO 5
<211> LENGTH: 700
<212> TYPE: DNA
<213> ORGANISM: Homo sapiens

<400> SEQUENCE: 5
catataaaag ctagtgcaga actcacagaa aatataagat ttaatatgcc ttgataagat       60
taatttaggg aaagttggcc atggattta gataatcata agtctttaat caaaattctg      120
tctatgggtt caaaaattaa catggttaat atacttttc atttctgaaa ttttacactt      180
actaaatata gattttggaa acttaagtat taatagaaat ttttttcctgg ttctcaaaac      240 aaaaaatttc tgatatctag gatcattctt atgccaaggc cttttgaaga cttttctttt      300
ctgggagtga tttgaaagga ttaaatttct ctttaggttg tacaagagta tgaaagagta      360
attatattcc gactgggaca tctgcttcct ggaagagcca aaggccctgg taaaaaaaca      420
```

```
ctcttttttt tctaaacacc tctctcctga cttgccaatt tcttcaaccc atgcagattt      480
gtaatatgga cctcagatta aatgaagtaa cttgattcat gatatctgaa ttttccaatc      540
tgttacttat aggttattca aatattcttc agagactatt actactaggt cataggtagc      600
caagagagag aattggtaca gagagcccac atgccagggc aaggcttgct ggaatagcaa      660
gttagcttag gaccaatggc tggggactga tgtgagtacg                            700
```

<210> SEQ ID NO 6
<211> LENGTH: 360
<212> TYPE: DNA
<213> ORGANISM: Homo sapiens
<220> FEATURE:
<221> NAME/KEY: misc_feature
<222> LOCATION: 327
<223> OTHER INFORMATION: where n may be either a or g or c or t/u,
      unknown or other

<400> SEQUENCE: 6

```
ctggattaca tattataata tataatagtg ctctcctttt accctcaggt ggaggtggga       60
tgggccaatg gtctgtaatt agaggctaag aaaagtaatg tagtgtgcaa cctgaccccca     120 gaaaggtgaa acccaaacag cyttcatgct agctatttat cygtcayttc ctcctcctct      180
cttttaggtc ttttctttt tttgccctgc ctggatacct accacaaggt tgaccttcgt      240
ctccaaactc tggagatacc ttttcatgag gtaagccaaa tgatggcttt tgctttctct      300
atacattttc catggtctac ctaccgngga caaaatgatt atttatactc aaaaatagga      360
```

<210> SEQ ID NO 7
<211> LENGTH: 649
<212> TYPE: DNA
<213> ORGANISM: Homo sapiens

<400> SEQUENCE: 7

```
cttcttatga gaagattatt tctgattttt tttacaaaag gatttaccac aggattaagt       60
tgtgcattct ttcgtgtatt taataaaaat ttcataattt tcaaaaacat gtctatttta      120
aataaagggt aggccaactc cattttctc ttgcggagaa aattcacttt gaacacattt       180
agttcctcta acccccacata ggaaaggagc ccaagaatca agcctgtcat ccaaactttt     240
ttctgcctag atcgtgacca aagacatgtt tataatggag atagatgcca tttgctacta      300
ccgaatggaa aatgcctctc ttctcctaag cagtcttgct catgtatcta aagctgtgca      360
attccttgtg caaaccacta tgaagcgtct cctagcacat cgatccctca ctgaaattct      420
tctagagagg aagagcatcg cccaagatgc aaaggtactt agataaacat aatggccaat      480
atgctgaaat atttatcttt tattcatttg ttcgttggac atttattaaa tcttctatgg      540
ccagttccat cccttagggg ccatcccttt gggagctcat agctagttag gaggttgcca      600
aattgactct gagtcaatta tagttatcag tatggtgctt gttaatcag                  649
```

<210> SEQ ID NO 8
<211> LENGTH: 592
<212> TYPE: DNA
<213> ORGANISM: Homo sapiens

<400> SEQUENCE: 8

```
aattacattt agggccacct ggataatcca ggataatatc cccatctcaa gagcctttaa       60
cctaatcaaa ccagcaaaat ccctcttggg gtaacattca cagattccag ggattaggac      120
atgggatatc tttggggacc attattcagc ataccacacc atcttcaatt gcacagatat      180
ttattgggtg gcaccatgca agttaaacaa ctctttgcaa ggcactgtga agttaaatac      240
```

| | |
|---|---|
| aacaggcaaa taatgtcctt tcaaagggaa tgttgttcct tagtacagaa caatggccac | 300 |
| cagggtttag gcatgctctc ctcccacctg gaggctccca ctgacatctg aattcttctt | 360 |
| tccacaggtt gccttggatt cagtgacctg tatttgggga atcaaagtgg agagaataga | 420 |
| aatgtgggta ggaaattaac tagcaagaac tgtatgataa aggaaaatat tctggtttca | 480 |
| ttttaaattt ttcatttgaa aaattatttt cactgagtac tatagccata tcagcataaa | 540 |
| tttataaaaa agagaaacaa atcacctaat atcttacagc ataacacaa tc | 592 |

<210> SEQ ID NO 9
<211> LENGTH: 716
<212> TYPE: DNA
<213> ORGANISM: Homo sapiens
<220> FEATURE:
<221> NAME/KEY: misc_feature
<222> LOCATION: 510
<223> OTHER INFORMATION: where n may be either a or g or c or t/u,
unknown or other

<400> SEQUENCE: 9

| | |
|---|---|
| cattgttcaa atttattagt tgggcttag attatatcct aagcggaaaa actgagcaca | 60 |
| gctcatcaaa tacaaaacct gctgtgctga taatgagaaa ctacagctct actgtagcat | 120 |
| cagcaataat acaaaactgc atttgaggca tcgaccttgg agatctgcct acttttgacc | 180 |
| tcagaagtct aggaatggca cactctggtc actccaaatt tgctactcat catgagacag | 240 |
| cagtagagag gcttgcaagt ctgtgtgaaa gctttggccc ctaaatcatg gctgcacacc | 300 |
| tacatacctg cattctttct ttttcagtaa agatgtgagg ttgccagctg ggcttcagca | 360 |
| ctcactggct gtggaggctg aagcgcaaag acaagccaaa gtgcgggtga gcactccatc | 420 |
| ctcccaccca gactgccctt taggaaggcc tgctcgtgga aacatttcc cctttgcttc | 480 |
| cttactgtcc attcattagg cactgggcan aagctgtctt gggcccttac aactctatta | 540 |
| aaattgctct cttaaagtgt gttaatagtc ccctgactaa tgcaactcct ctccctctct | 600 |
| gaagctactg ataatagtga ccactcactg cttgagtctc accttccctc tctctcctta | 660 |
| aaggcatctc ctccacacac atcaatccct cttctctagt gctggcatct tttcct | 716 |

<210> SEQ ID NO 10
<211> LENGTH: 1305
<212> TYPE: DNA
<213> ORGANISM: Homo sapiens

<400> SEQUENCE: 10

| | |
|---|---|
| ggcaaaatcc taatctttca aggcccacca gatgctaata actcccctaa tacttcattt | 60 |
| atacttgtga tggctcctaa cgcattccac cttaaattgt gattaacagt ttaatctgtc | 120 |
| tccccagctc aagacccttc agaaagaaga ataaacatgt tctatgctta accgtgcttg | 180 |
| ccacatagta gatgctcagt gcttgtctgc tgagtcatac tgcatagtgg tgaagccttc | 240 |
| agggaatgaa gaacaatcac tttgctttcg tcacatgttt tctagatgat tgctgcagaa | 300 |
| gcggaaaagg ctgcttctga gtccctgagg atggcagctg agattctgtc aggcaccct | 360 |
| gctgctgttc agcttcgata cctccacacc cttcagtctc tgtccacaga gaagccttcc | 420 |
| actgtggttt tacctttgcc atttgaccta ctgaattgcc tgtcttctcc cagcaacaga | 480 |
| actcagggaa gcctcccctt cccaagtcct tccaaacctg ttgagccact aaatcctaaa | 540 |
| aagaaagact ctcccatgtt ataggaagga tggggcataa tgtgactgta aaggggcctg | 600 |
| ccatagaaaa gtcacatccc tgagggagac actctgtcct cattccctgc ccttccttg | 660 |

| | |
|---|---|
| gttgccatat ggaatggcca tggaatgcac gaagtcacaa tgcaccatcc atgagaagac | 720 |
| rgtgaaatga tgtaatgaca gagaaggcag acaacatgtt tccgtgactc atctagtcag | 780 |
| agcaattatg ggaaacagct ttggtcaaca ttctactttg graagaattt tgagtctaga | 840 |
| tgtggttaaa ttttgacttc tgggaacttg gttcagatgt cccttcact gtatgtcctc | 900 |
| tgaccccttt ggcaaggttg ccacagctcc cacagccctt cctacaagca cctatcattg | 960 |
| ggcttgtcac actctattgc tcttctgtcc craagatgca gtcttctctc caatgatact | 1020 |
| accaagtctt agttttcctc aaccacactc aatcttttg ctccaccctg aattcctcac | 1080 |
| acctaaccct gatagttacc taaagtgaca cttaaatgtt tcagagtgaa tgcaaaaaag | 1140 |
| agagatgtac ttggagtcgg atatacaatt tatccctaat taaagcattt aaaaggaatt | 1200 |
| cttttttgtgg agattccttt tttaaacaaa taaataaaag gacaaaaaca tctgacacat | 1260 |
| gtggcttaaa atctgaggga gaatcactat aaatagtggg ccaga | 1305 |

<210> SEQ ID NO 11
<211> LENGTH: 1065
<212> TYPE: DNA
<213> ORGANISM: Homo sapiens

<400> SEQUENCE: 11

| | |
|---|---|
| ccactatgaa gcgtctccta gcacatcgat ccctcactga aattcttcta gagaggaaga | 60 |
| gcatcgccca agatgcaaag gttgccttgg attcagtgac ctgtatttgg ggaatcaaag | 120 |
| tggagagaat agaaattaaa gatgtgaggt tgccagctgg gcttcagcac tcactggctg | 180 |
| tggaggctga agcgcaaaga caagccaaag tgcggatgat tgctgcagaa gcggaaaagg | 240 |
| ctgcttctga gtccctgagg atggcagctg agattctgtc aggcaccct gctgctgttc | 300 |
| agcttcgata cctccacacc cttcagtctc tgtccacaga gaagccttcc actgtggttt | 360 |
| tacctttgcc atttgaccta ctgaattgcc tgtcttctcc cagcaacaga actcagggaa | 420 |
| gcctccccttt cccaagtcct tccaaacctg ttgagccact aaatcctaaa agaaagact | 480 |
| ctcccatgtt ataggaagga tggggcataa tgtgactgta aaggggcctg ccatagaaaa | 540 |
| gtcacatccc tgagggagac actctgtcct cattccctgc ccttcctttg gttgccatat | 600 |
| ggaatggcca tggaatgcac gaagtcacaa tgcaccatcc atgagaagac agtgaaatga | 660 |
| tgtaatgaca gagaaggcag acaacatgtt tccgtgactc atctagtcag agcaattatg | 720 |
| ggaaacagct ttggtcaaca ttctactttg gaaagaattt tgagtctaga tgtggttaaa | 780 |
| ttttgacttc tgggaacttg gttcagatgt cccttcact gtatgtcctc tgaccccttt | 840 |
| ggcaaggttg ccacagctcc cacagccctt cctacaagca cctatcattg ggcttgtcac | 900 |
| actctattgc tcttctgtcc cgaagatgca gtcttctctc caatgatact accaagtctt | 960 |
| agttttcctc aaccacactc aatcttttg ctccaccctg aattcctcac acctaaccct | 1020 |
| gatagttacc taaagtgaca cttaaatgtt tcagagtgaa tgcaa | 1065 |

<210> SEQ ID NO 12
<211> LENGTH: 20
<212> TYPE: DNA
<213> ORGANISM: Homo sapiens

<400> SEQUENCE: 12

| | |
|---|---|
| gcagcgactc cacagggact | 20 |

<210> SEQ ID NO 13
<211> LENGTH: 20

```
<212> TYPE: DNA
<213> ORGANISM: Homo sapiens

<400> SEQUENCE: 13
tcagtgggtc tcgtggggat                                              20

<210> SEQ ID NO 14
<211> LENGTH: 20
<212> TYPE: DNA
<213> ORGANISM: Homo sapiens

<400> SEQUENCE: 14
aggcagtgaa tacagtgaag                                              20

<210> SEQ ID NO 15
<211> LENGTH: 19
<212> TYPE: DNA
<213> ORGANISM: Homo sapiens

<400> SEQUENCE: 15
ggcctcagga aattaccta                                               19

<210> SEQ ID NO 16
<211> LENGTH: 20
<212> TYPE: DNA
<213> ORGANISM: Homo sapiens

<400> SEQUENCE: 16
ttctgggagt gatttgaaag                                              20

<210> SEQ ID NO 17
<211> LENGTH: 20
<212> TYPE: DNA
<213> ORGANISM: Homo sapiens

<400> SEQUENCE: 17
tgaagaaatt ggcaagtcag                                              20

<210> SEQ ID NO 18
<211> LENGTH: 19
<212> TYPE: DNA
<213> ORGANISM: Homo sapiens

<400> SEQUENCE: 18
aaggtgaaac ccaaacagc                                               19

<210> SEQ ID NO 19
<211> LENGTH: 20
<212> TYPE: DNA
<213> ORGANISM: Homo sapiens

<400> SEQUENCE: 19
cggtaggtag accatggaaa                                              20

<210> SEQ ID NO 20
<211> LENGTH: 20
<212> TYPE: DNA
<213> ORGANISM: Homo sapiens

<400> SEQUENCE: 20
cataggaaag gagcccaaga                                              20

<210> SEQ ID NO 21
```

```
<211> LENGTH: 20
<212> TYPE: DNA
<213> ORGANISM: Homo sapiens

<400> SEQUENCE: 21
tttcagcata ttggccatta                                                 20

<210> SEQ ID NO 22
<211> LENGTH: 17
<212> TYPE: DNA
<213> ORGANISM: Homo sapiens

<400> SEQUENCE: 22
ctcccactga catctga                                                    17

<210> SEQ ID NO 23
<211> LENGTH: 20
<212> TYPE: DNA
<213> ORGANISM: Homo sapiens

<400> SEQUENCE: 23
aatttaaaat gaaaccagaa                                                 20

<210> SEQ ID NO 24
<211> LENGTH: 20
<212> TYPE: DNA
<213> ORGANISM: Homo sapiens

<400> SEQUENCE: 24
ctaaatcatg gctgcacacc                                                 20

<210> SEQ ID NO 25
<211> LENGTH: 20
<212> TYPE: DNA
<213> ORGANISM: Homo sapiens

<400> SEQUENCE: 25
cttcctaaag ggcagtctgg                                                 20

<210> SEQ ID NO 26
<211> LENGTH: 20
<212> TYPE: DNA
<213> ORGANISM: Homo sapiens

<400> SEQUENCE: 26
ggtgaagcct tcagggaatg                                                 20

<210> SEQ ID NO 27
<211> LENGTH: 20
<212> TYPE: DNA
<213> ORGANISM: Homo sapiens

<400> SEQUENCE: 27
ttctatggca ggcccctta                                                  20

<210> SEQ ID NO 28
<211> LENGTH: 1652
<212> TYPE: DNA
<213> ORGANISM: Rattus rattus
<220> FEATURE:
<221> NAME/KEY: CDS
<222> LOCATION: (47)..(1195)

<400> SEQUENCE: 28
```

-continued

| | |
|---|---|
| cgactctgcc agcatctggc tttgggggggc gtgcccgccg cgtaga atg gac agc<br>                                             Met Asp Ser<br>                                              1 | 55 |
| agg gcg cgg agc tct tcc aga aag acc cac ggg aga ggt agc agg tcc<br>Arg Ala Arg Ser Ser Ser Arg Lys Thr His Gly Arg Gly Ser Arg Ser<br> 5          10          15 | 103 |
| tct tct agg gat gac aag aag tca aag gcc ggg agg ggc aac aga ggc<br>Ser Ser Arg Asp Asp Lys Lys Ser Lys Ala Gly Arg Gly Asn Arg Gly<br>20         25         30         35 | 151 |
| cgc gcg cgc ccg gat gct ggg gca gag cgg cag agc gcc ggg cgg acg<br>Arg Ala Arg Pro Asp Ala Gly Ala Glu Arg Gln Ser Ala Gly Arg Thr<br>         40         45         50 | 199 |
| ggg acc cgg gag gag cac cga gct cca gca gcc acg gta gtg aat gtg<br>Gly Thr Arg Glu Glu His Arg Ala Pro Ala Ala Thr Val Val Asn Val<br>     55          60         65 | 247 |
| gac gag gtt cga agc ccg ggt gag gag ggt acg gaa gtg gtg gcc ctg<br>Asp Glu Val Arg Ser Pro Gly Glu Glu Gly Thr Glu Val Val Ala Leu<br>       70         75         80 | 295 |
| ctg gag agc gag cga cca gag gaa ggg atc aag ccc tct gga tta ggg<br>Leu Glu Ser Glu Arg Pro Glu Glu Gly Ile Lys Pro Ser Gly Leu Gly<br>85         90         95 | 343 |
| gcc tgc gag tgg ctt ctt gtc ctc tcc tcc ctg atc ttc atc atc gta<br>Ala Cys Glu Trp Leu Leu Val Leu Ser Ser Leu Ile Phe Ile Ile Val<br>100        105        110        115 | 391 |
| acg ttt ccc ttt tcc atc tgg ttc tgc ata aag gtt gtt caa gaa tac<br>Thr Phe Pro Phe Ser Ile Trp Phe Cys Ile Lys Val Val Gln Glu Tyr<br>         120        125        130 | 439 |
| gaa aga gta att ata ttc cga ctg gga cat ctg ctt cct gga aga gcc<br>Glu Arg Val Ile Ile Phe Arg Leu Gly His Leu Leu Pro Gly Arg Ala<br>     135          140        145 | 487 |
| aaa gga cct ggc ctg ttc ttt ttt cta ccc tgc ctg gac acc tat cac<br>Lys Gly Pro Gly Leu Phe Phe Phe Leu Pro Cys Leu Asp Thr Tyr His<br>       150         155        160 | 535 |
| aag gtt gac ctc cgt ctc cag acc ttg gaa ata cct ttc cat gag gtg<br>Lys Val Asp Leu Arg Leu Gln Thr Leu Glu Ile Pro Phe His Glu Val<br>165        170        175 | 583 |
| gta acc aaa gat atg ttc aca atg gag ata gac gct gtc tgc tac tac<br>Val Thr Lys Asp Met Phe Thr Met Glu Ile Asp Ala Val Cys Tyr Tyr<br>180        185        190        195 | 631 |
| cgc atg gaa aat gcc tcc ctt ctt cta agc agt cta gct cat gtg tcc<br>Arg Met Glu Asn Ala Ser Leu Leu Leu Ser Ser Leu Ala His Val Ser<br>         200        205        210 | 679 |
| aaa gcc atc cag ttc ctg gtg caa acc acc atg aag cgc ctc ttg gca<br>Lys Ala Ile Gln Phe Leu Val Gln Thr Thr Met Lys Arg Leu Leu Ala<br>     215          220        225 | 727 |
| cat cga tcc ctc act gaa att ctc ctg gaa agg aag agc att gcc caa<br>His Arg Ser Leu Thr Glu Ile Leu Leu Glu Arg Lys Ser Ile Ala Gln<br>       230         235        240 | 775 |
| gat gta aag gtt gcc ttg gac tca gtg acc tgt gtt tgg ggc atc aaa<br>Asp Val Lys Val Ala Leu Asp Ser Val Thr Cys Val Trp Gly Ile Lys<br>245        250        255 | 823 |
| gtg gag aga act gaa att aag gat gta cgg ctg cca gct ggg ctt cag<br>Val Glu Arg Thr Glu Ile Lys Asp Val Arg Leu Pro Ala Gly Leu Gln<br>260        265        270        275 | 871 |
| cac tct ctg gct gtg gaa gct gag gca caa aga cag gcc aaa gtg cgg<br>His Ser Leu Ala Val Glu Ala Glu Ala Gln Arg Gln Ala Lys Val Arg<br>         280        285        290 | 919 |
| gtg att gct gcc gaa ggg gaa aaa gct gcc tct gag tcc ctg agg atg<br>Val Ile Ala Ala Glu Gly Glu Lys Ala Ala Ser Glu Ser Leu Arg Met<br>     295          300        305 | 967 |

-continued

| | | | | | | | | | | | |
|--|--|--|--|--|--|--|--|--|--|--|--|
| gcg | gct | gag | att | ctg | tca | ggc | acc | cca | gct | gct | gtc | cag | ctc | cgg | tac | 1015 |
| Ala | Ala | Glu | Ile | Leu | Ser | Gly | Thr | Pro | Ala | Ala | Val | Gln | Leu | Arg | Tyr |
| | 310 | | | | | 315 | | | | | 320 | | | | |

```
gcg gct gag att ctg tca ggc acc cca gct gct gtc cag ctc cgg tac     1015
Ala Ala Glu Ile Leu Ser Gly Thr Pro Ala Ala Val Gln Leu Arg Tyr
        310                 315                 320 ctg cac act ctt cag tcc ttg tcc aca gac aag ccg tcc acc gtg gtt     1063
Leu His Thr Leu Gln Ser Leu Ser Thr Asp Lys Pro Ser Thr Val Val
    325                 330                 335 ttg cct tta ccc ttt gac atg ctg aac ctt ctc tcc tct ccc agc aac     1111
Leu Pro Leu Pro Phe Asp Met Leu Asn Leu Leu Ser Ser Pro Ser Asn
340                 345                 350                 355 aga gca caa gga agc atc aac tac cca agt tct ccc aaa cct gtt gaa     1159
Arg Ala Gln Gly Ser Ile Asn Tyr Pro Ser Ser Pro Lys Pro Val Glu
                360                 365                 370 cca cta aat ccc aaa agg aag gac tct cct atg cta tagggcgag           1205
Pro Leu Asn Pro Lys Arg Lys Asp Ser Pro Met Leu
                375                 380 tggacaagag taatgggaat acaccatata aagccgtatc cctgagcgag gcattcggtc   1265
cccacgccca ggcccaccct gcccttgttg tttgccttt t gagtgtatca tgtcacaaga  1325
tggacacacg catgagaaca cagtgaaatg gcagagaaga catccagcca cacaagtggg   1385
tcgtctcatc attcattaca ggaaagaaag agatttagaa ttttggttg aggggctgga    1445 gagatggctc agtggttatg aacactgact gctcttccag aggtcctgag ttcaaatccc   1505
agcaaccaca tggtggctca caaccatctg taatgggatc cgatgccctc ttctggtgtg   1565
taagacagtg acagtgtact catcatatat aagatgaata aataaaccct tttaaaaaaa   1625
aaaaaaaaaa aaaaaaaaaa aaaaaaa                                       1652

<210> SEQ ID NO 29
<211> LENGTH: 383
<212> TYPE: PRT
<213> ORGANISM: Rattus rattus

<400> SEQUENCE: 29

Met Asp Ser Arg Ala Arg Ser Ser Arg Lys Thr His Gly Arg Gly
  1               5                  10                  15

Ser Arg Ser Ser Arg Asp Asp Lys Lys Ser Lys Ala Gly Arg Gly
             20                  25                  30

Asn Arg Gly Arg Ala Arg Pro Asp Ala Gly Ala Glu Arg Gln Ser Ala
         35                  40                  45

Gly Arg Thr Gly Thr Arg Glu Glu His Arg Ala Pro Ala Ala Thr Val
     50                  55                  60

Val Asn Val Asp Glu Val Arg Ser Pro Gly Glu Gly Thr Glu Val
 65                  70                  75                  80

Val Ala Leu Leu Glu Ser Glu Arg Pro Glu Gly Ile Lys Pro Ser
                 85                  90                  95

Gly Leu Gly Ala Cys Glu Trp Leu Leu Val Leu Ser Ser Leu Ile Phe
            100                 105                 110

Ile Ile Val Thr Phe Pro Phe Ser Ile Trp Phe Cys Ile Lys Val Val
        115                 120                 125

Gln Glu Tyr Glu Arg Val Ile Ile Phe Arg Leu Gly His Leu Leu Pro
    130                 135                 140

Gly Arg Ala Lys Gly Pro Gly Leu Phe Phe Leu Pro Cys Leu Asp
145                 150                 155                 160

Thr Tyr His Lys Val Asp Leu Arg Leu Gln Thr Leu Glu Ile Pro Phe
                165                 170                 175

His Glu Val Val Thr Lys Asp Met Phe Thr Met Glu Ile Asp Ala Val
```

-continued

```
                180                 185                 190
Cys Tyr Tyr Arg Met Glu Asn Ala Ser Leu Leu Leu Ser Ser Leu Ala
        195                 200                 205

His Val Ser Lys Ala Ile Gln Phe Leu Val Gln Thr Thr Met Lys Arg
        210                 215                 220

Leu Leu Ala His Arg Ser Leu Thr Glu Ile Leu Leu Glu Arg Lys Ser
225                     230                 235                 240

Ile Ala Gln Asp Val Lys Val Ala Leu Asp Ser Val Thr Cys Val Trp
                245                 250                 255

Gly Ile Lys Val Glu Arg Thr Glu Ile Lys Asp Val Arg Leu Pro Ala
                260                 265                 270

Gly Leu Gln His Ser Leu Ala Val Glu Ala Glu Ala Gln Arg Gln Ala
        275                 280                 285

Lys Val Arg Val Ile Ala Ala Glu Gly Glu Lys Ala Ala Ser Glu Ser
        290                 295                 300

Leu Arg Met Ala Ala Glu Ile Leu Ser Gly Thr Pro Ala Ala Val Gln
305                     310                 315                 320

Leu Arg Tyr Leu His Thr Leu Gln Ser Leu Ser Thr Asp Lys Pro Ser
                325                 330                 335

Thr Val Val Leu Pro Leu Pro Phe Asp Met Leu Asn Leu Leu Ser Ser
                340                 345                 350

Pro Ser Asn Arg Ala Gln Gly Ser Ile Asn Tyr Pro Ser Ser Pro Lys
        355                 360                 365

Pro Val Glu Pro Leu Asn Pro Lys Arg Lys Asp Ser Pro Met Leu
        370                 375                 380
```